United States Patent [19]

Smith et al.

[11] 3,953,510

[45] Apr. 27, 1976

[54] METHOD FOR THE PREPARATION OF ALKOXYANILINES

[75] Inventors: Curtis P. Smith, Cheshire, Conn.; Peter H. Scott, Sudbury, Mass.

[73] Assignee: Olin Corporation, New Haven, Conn.

[22] Filed: June 27, 1974

[21] Appl. No.: 483,605

Related U.S. Application Data

[63] Continuation of Ser. No. 248,898, May 1, 1972, abandoned, which is a continuation-in-part of Ser. No. 8,060, Feb. 2, 1970, abandoned.

[52] U.S. Cl.................................. 260/580; 260/575
[51] Int. Cl.².......................................... C07C 85/10
[58] Field of Search............................ 260/575, 580

[56] References Cited
UNITED STATES PATENTS 3,558,707   1/1971   Churchill et al................... 260/580
3,580,951   5/1971   Churchill et al................... 260/580

OTHER PUBLICATIONS

Houben–Weyl, "Methoden Der Organischen Chemie", Vol. 613, 4th Ed., pp. 75–79, (1965).

Migrdichian Organic Synthesis, Vol. II, pp. 1571 and 1578 (1957).

Primary Examiner—Helen M. S. Sneed
Attorney, Agent, or Firm—Kenneth P. Glynn; Eugene Zagarella, Jr.

[57] ABSTRACT

Alkoxyanilines are prepared in a one-step operation by reacting selected nitrobenzenes with selected alcohols and a deoxygenating agent in the presence of anhydrous hydrogen fluoride.

13 Claims, No Drawings

METHOD FOR THE PREPARATION OF ALKOXYANILINES

This application is a Continuation of Ser. No. 248,898, filed May 1, 1972 which is a continuation-In-Part of Ser. No. 8,060, filed Feb. 2, 1970 both now abandoned.

This invention relates to the one-step method of preparation of alkoxyanilines. More particularly, it relates to a process in which selected nitrobenzenes are reacted with selected alcohols in the presence of a deoxygenating agent and anhydrous hydrogen fluoride.

The product alkoxyanilines are valuable compounds which are useful as dyestuffs or coloring agents (See Chemical Abstracts, Vol. 51, P4008d, 1957), as antipyretic agents and in the preparation of surfactants.

Previous methods of preparing alkoxyanilines from nitrobenzenes generally involved an indirect route to such compounds by prior reduction of nitrobenzene to a suitable material such as N-aryl hydroxylamine and phenylazide and then reacting such material with ethanol in sulfuric acid as described by E. Bamberger in Liebig's Annalen die Chemie 424, 233 (1921).

The method of this invention is particularly advantageous because it provides alkoxyanilines by a direct one-step conversion from inexpensive starting materials thus obviating any prior reaction or reduction steps.

Broadly stated, the process of this invention involves reaction of selected nitrobenzenes with selected alcohols in the presence of a deoxygenating agent and anhydrous hydrogen fluoride as for example, shown by the following equation wherein nitrobenzene is reacted with ethanol in the presence of triphenyl phosphine and anhydrous hydrogen fluoride:

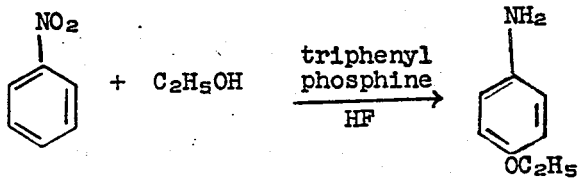

Generally, the alkoxy substituent will take either the para or one of the ortho positions to the reduced nitro group and preferably the para position.

Suitable nitrobenzenes for use as starting material include nitrobenzene and substituted nitrobenzenes having as an additional substituent on the benzene ring at least one of the following: alkyl and more particularly alkyl of 1 to 4 carbon atoms, for example, methyl, ethyl and butyl; halogen, for example, chlorine, fluorine, bromine and iodine; and additional nitro groups on the benzene ring. It is further noted that on the selected nitrobenzene compound at least one of the para or the ortho positions to the nitro group must be unsubstituted. Examples of nitrobenzenes suitable as starting material include but are not limited to the following: nitrobenzene, m-nitrobenzene, o-nitrotoluene, m-ethylnitrobenzene, 2,6-dimethylnitrobenzene, 4-methyl-1,3-dinitrobenzene, m-chloronitrobenzene, o-chloronitrobenzene, m-bromonitrobenzene, o-fluoronitrobenzene, m-iodonitrobenzene, 2,5-dichloronitrobenzene, 2,5-difluoronitrobenzene, m-dinitrobenzene, o-dinitrobenzene and p-dinitrobenzene.

Suitable alcohols which may be used include saturated and unsaturated aliphatic alcohols and more particularly unsubstituted, branched and unbranched, hydroxyalkyl and hydroxyalkenyl compounds containing from 1 to 8 and preferably from 1 to 4 carbon atoms. Alcohols of the above type may contain up to three hydroxyl groups with the monohydric alcohols and diols being preferred. Additional alcohols which may be used include the alcohols of polyoxyalkylene glycol ethers having the formula:

wherein R is an alkyl of 1 to 4 carbons preferably 1 to 2 or a hydroxyl group; $R_1$ is an ethylene or propylene group and x is 1 to 20 and preferably 1 to 4. It is further noted that the alkylene group may contain an additional hydroxyl group if desired. Preferred alcohols of this type are the polyoxyalkylene glycol monoalkyl ethers.

Illustrative of the above type alcohols are the following compounds: methanol, ethanol, propanol, isopropanol, butanol, isobutanol, tertiary butanol, octanol, allyl alcohol, methallyl alcohol, 2-ethyl-3-methyl-1-butanol, 2,4-hexanediol, ethylene glycol, glycerol, ethylene glycol monomethyl ether, diethylene glycol monomethyl ether, diethylene glycol monoethyl ether, triethylene glycol monomethyl ether and decaethylene glycol monomethyl ether. Further illustrations of the above type compounds may be found in "Organic Chemistry" by Cram and Hammond, 1959.

Deoxygenating agents which may be used include (1) elemental phosphorus and sulfur; (2) phosphorus and sulfur halides including the fluorides, chlorides, bromides and iodides of trivalent phosphorus and of sulfur lower in valence than 6, for example, phosphorus trifluoride, phosphorus trichloride, sulfur chloride, sulfur dichloride, sulfur tetrachloride, sulfur bromide, sulfur iodide, phosphorus, tri-iodide and sulfur tetrafluoride; (3) aryl and diaryl phosphorus and sulfur halides wherein such aryl groups preferably have 6 to 10 carbon atoms, for example, diphenyl phosphorus chloride, di-p-tolyl phosphorus chloride, benzene sulfenyl chloride and p-tolyl sulfenyl bromide; and (4) triaryl phosphines and more particularly triaryl phosphines wherein the aryl group has 6 to 10 carbon atoms, for example, triphenyl phosphine, tri-o-tolyl phosphine, tri-p-tolyl phosphine, tri-m-tolyl phosphine, tri-p-bromophenyl phosphine, tri-p-chlorophenyl phosphine, tri-(2,4-dimethylphenyl) phosphine, tri-(4-ethylphenyl)phosphine and β-naphthyl diphenyl phosphine.

Generally, a molar ratio of hydrogen fluoride to the selected nitrobenzene of at least 1:1 is used and molar ratios up to 50:1 are suitable but more hydrogen fluoride can be used, if desired. Ratios of less than 1:1 can be used but the yield will suffer. Preferably molar ratios of 1:1 to 30:1 are used.

The ratio of deoxygenating agent to the selected nitrobenzene is generally in the 0.3:1 to 5:1 range with the preferable range being 0.5:1 to 2:1.

The ratio of selected alcohol to the selected nitrobenzene is generally at least 1:1 since it is desirable to have some excess alcohol. The ratio may go up to 50:1 or even higher with the preferred range being 2:1 up to 30:1.

The temperature at which the reaction is carried out may generally be from 20° to 250°C. with the preferred range being 90° to 165°C.

The pressure used is suitably autogenous and may generally vary from 0 to 10,000 psig. with the preferred range being 0 to 500 psig.

The time required for the reaction will vary widely with different deoxygenating agents. Satisfactory yields will be obtained generally in 1 to 12 hours.

After the reaction is completed, the product is isolated in any convenient manner. For example, excess hydrogen fluoride is evaporated or distilled off. Water is added and the oxidation product together with unconverted deoxygenating agent, both of which are usually insoluble in water, are filtered off or otherwise separated. The aqueous layer is made alkaline and the liberated anilines are separated and/or extracted with any suitable water immiscible organic solvent, for example, ether. The ether is dried and distilled to recover the alkoxyaniline product.

The following examples are illustrative of this invention.

EXAMPLE I

A 100 ml. Hastelloy B rocking autoclave was charged with 3.10 g. (.025 mole) of nitrobenzene, 13.10 g. (0.05 mole) of triphenyl phosphine, 4.60 g. (0.10 mole) ethanol and 10 g. (0.5 mole) of anhydrous HF. The mixture was heated to 150°C. at 150 psig. autogenous pressure and maintained at that temperature for 3 hours. After cooling, the contents of the autoclave were discharged into a plastic beaker and most of the HF was evaporated, using a nitrogen sparge. The residue was triturated with water and filtered to remove insolubles, mainly triphenyl phosphine oxide. After addition of cold 15 percent KOH to the filtrate, the acid soluble material (3.2 gm) thus liberated was recovered by ether extracting. Vapor phase chromatographic (VPC) analysis gave the following product distribution: 60.6 mole percent total anilines (at 95% nitrobenzene conversion) which consists of p-ethoxyaniline, 27.2 mole %; o-ethoxyaniline, 3.3 mole %; p-fluoroaniline, 35.6 mole %; o-fluoroaniline, 1.2 mole %; aniline, 32.7 mole %.

EXAMPLE II

The same procedure as in Example I was followed using 3.1 g. (0.025 mole) of nitrobenzene, 13.1 g. (0.05 mole) of triphenyl phosphine, 2.3 g. (0.05 mole) of ethanol and 10 g. (0.5 mole) of anhydrous HF. VPC analysis gave the following product distribution: 45.9 mole percent total anilines (at 96 percent nitrobenzene conversion) which included 12.5 mole percent of p-ethoxyaniline; 57.1 mole percent of p-fluoroaniline.

EXAMPLE III

The same procedure as in Example I was followed using 3.1 g. (0.025 mole) of nitrobenzene, 13.1 g. (0.05 mole) of triphenyl phosphine, 9.25 g. (0.2 mole) of ethanol and 4 g. (0.2 mole) of anhydrous HF. VPC analysis gave the following product distribution: 32.0 mole percent total anilines (at 96 percent nitrobenzene conversion) which included 52.6 mole percent of p-ethoxyaniline; 10.2 mole percent of p-fluoroaniline.

EXAMPLE IV

The same procedure as in Example I was followed using 3.1 g. (0.025 mole) of nitrobenzene, 13.1 g. (0.05 mole) of triphenyl phosphine, 3.2 g. (0.1 mole) of methanol and 10 g. (0.5 mole) of anhydrous HF. VPC analysis gave the following product distribution: 53.0 mole percent total anilines (at approximately 95 percent nitrobenzene conversion) which included 29.1 mole percent of p-methoxyaniline; 35.8 percent of p-fluoroaniline.

EXAMPLE V

The same procedure as in Example I was followed using 3.1 g. (0.025 mole) of nitrobenzene, 13.1 g. (0.05 mole) of triphenyl phosphine, 6.01 g. (0.1 mole) of propanol and 10 g. (0.5 mole) of anhydrous HF. VPC analysis gave the following product distribution: 49.7 mole percent of total anilines (at 98 percent nitrobenzene conversion) which included 26.7 mole percent of p-propoxyaniline; 37.8 mole percent of p-fluoroaniline.

What is claimed is:

1. A method for preparing an o- or p- alkoxyaniline or substituted o- or p- alkoxyaniline which comprises reacting at a temperature of from about 20° to about 250°C. a mixture of
   a. a nitrobenzene selected from the group consisting of nitrobenzene and substituted nitrobenzene having as an additional substituent on the benzene ring at least one of the following: alkyl of 1 to 4 carbon atoms, halogen and nitro, with the proviso that at least one of the para or ortho positions to the nitro group is unsubstituted;
   b. an alcohol selected from the group consisting of unsubsituted, branched and unbranched, hydroxyalkyl and hydroxyalkenyl alcohols of 1 to 8 carbon atoms and polyoxyalkylene glycol ether alcohols of the formula:

wherein R is an alkyl of 1 to 4 carbon atoms, $R_1$ is an ethylene or propylene group and x is 1 to 20;
   c. a deoxygenating agent selected from the group consisting of phosphorus, sulfur, phosphorus trihalides, sulfur halides in which sulfur has a valence lower than 6, aryl and diaryl phosphorus halides and aryl and diaryl sulfur halides, wherein the aryl group contains 6 to 10 carbon atoms, and triaryl phosphines wherein the aryl group contains 6 to 10 carbon atoms; and
   d. anhydrous hydrogen fluoride,
   said mixture containing a molar ratio of from about 1:1 to about 50:1 of said alcohol to said selected nitrobenzene, a molar ratio of from about 0.3:1 to about 5:1 of said deoxygenating agent to said selected nitrobenzene and a molar ratio of about 1:1 to about 50:1 of said hydrogen fluoride to said selected nitrobenzene and then separating said resulting o- or p- alkoxyaniline or o- or p- substituted alkoxyaniline from the reaction mixture.

2. The method of claim 1 wherein said deoxygenating agent is triphenyl phosphine.

3. The method of claim 1 wherein the molar ratio of alcohol to selected nitrobenzene is from about 2:1 to about 30:1.

4. The method of claim 1 wherein the molar ratio of hydrogen fluoride to selected nitrobenzene is from about 1:1 to about 30:1.

5. The method of claim 1 wherein the molar ratio of deoxygenating agent to selected nitrobenzene is from about 0.5:1 to about 2:1.

6. The method of claim 1 wherein nitrobenzene is reacted with ethanol to form p-ethoxyaniline.

7. The method of claim 1 wherein nitrobenzene is reacted with methanol to form p-methoxyaniline.

8. The method of claim 1 wherein nitrobenzene is reacted with propanol to form p-propoxyaniline.

9. The method of claim 1 wherein said temperature is from about 90° to about 165°C.

10. The method of claim 1 wherein said alcohol is an hydroxyalkyl alcohol of 1 to 8 carbon atoms.

11. The method of claim 1 wherein said mixture contains a molar ratio of from about 2:1 to about 30:1 of said alcohol to said selected nitrobenzene, a molar ratio of from about 0.5:1 to about 2:1 of said deoxygenating agent to said selected nitrobenzene and a molar ratio of from about 1:1 to about 30:1 of said hydrogen fluoride to said selected nitrobenzene.

12. The method of claim 1 wherein said alcohol is selected from the group consisting of unsubstituted, branched and unbranched, hydroxyalkyl and hydroxyalkenyl alcohols of 1 to 8 carbon atoms.

13. The method of claim 12 wherein said alcohol contains 1 to 4 carbon atoms.

* * * * *